United States Patent [19]

Ito et al.

[11] Patent Number: 5,709,849
[45] Date of Patent: Jan. 20, 1998

[54] SUPPRESSING STICKINESS TO SKIN OF COSMETIC COMPOSITION

[75] Inventors: Kenzo Ito; Shoji Nishiyama, both of Yokohama, Japan

[73] Assignee: Shiseido Company Ltd, Tokyo, Japan

[21] Appl. No.: 940,731

[22] Filed: Sep. 3, 1992

Related U.S. Application Data

[63] Continuation of Ser. No. 583,780, Sep. 17, 1990.

[30] Foreign Application Priority Data

Sep. 20, 1989 [JP] Japan .................................. 1-244779

[51] Int. Cl.⁶ .............................. A61K 7/02; A61K 7/48
[52] U.S. Cl. .............................. 424/63; 424/401
[58] Field of Search ............... 424/63, 401; 514/784, 514/873, 844–847; A61K 7/021, 7/48, 7/02

[56] References Cited

U.S. PATENT DOCUMENTS

| | | | |
|---|---|---|---|
| 4,606,913 | 8/1986 | Aronson et al. | 424/63 X |
| 5,002,761 | 3/1991 | Mueller et al. | 514/772 X |

FOREIGN PATENT DOCUMENTS

| | | | |
|---|---|---|---|
| 58-88304 | 5/1983 | Japan . | |
| 59-219212 | 12/1984 | Japan . | |
| 60-184571 | 9/1985 | Japan | 424/63 |

OTHER PUBLICATIONS

Abstract, Method for Blending Phospholipid Stably; 62–263109 (A) Appl. No. 61-102140; 25 C 493.

*Primary Examiner*—Neil S. Levy
*Attorney, Agent, or Firm*—Sprung Kramer Schaefer & Briscoe

[57] ABSTRACT

A cosmetic composition containing (i) a water-soluble polyhydric alcohol having two or more hydroxyl groups and/or a lecithin and (ii) a bivalent metal salt of an organic acid.

5 Claims, No Drawings

SUPPRESSING STICKINESS TO SKIN OF COSMETIC COMPOSITION

This application is a continuation or application Ser. No. 07/583,780, filed Sep. 17, 1990.

BACKGROUND OF THE INVENTION

1. Field of the Invention

The present invention relates to a cosmetic composition having the suppressed stickiness in feeling of use caused by water-soluble polyhydric alcohols and/or lecithins.

2. Description of the Related Art

The retention of moisture in the skin is an essential factor for keeping skin healthy, and numerous cosmetics and pharmaceuticals directed to moisture retention are available on the market. Active research is also underway on substances giving moisture retention and numerous moisture retention agents have been proposed. Water-soluble polyhydric alcohols and lecithins are superior in water retention and moisture absorption and, therefore, they are widely used for cosmetics, pharmaceuticals, and the like.

However, these water-soluble polyhydric alcohols and lecithins have the superior action of keeping the skin healthy and of restoring rough skin to normal, but are considerably sticky in feeling of use, which is a major problem in cosmetics, where the feeling of use desirably is good.

In view of the above-mentioned situation, the present inventors engaged in deep and extensive research to obtain a cosmetic composition having a high moisture retention effect superior in feeling of use and, as a result, discovered that the stickiness in question can be suppressed by mixing in a bivalent metal salt of organic acid in a cosmetic composition including water-soluble polyhydric alcohols and/or lecithins.

SUMMARY OF THE INVENTION

Accordingly, the objects of the present invention are to eliminate the above-mentioned disadvantages of the prior art and to provide a cosmetic composition having a superior moisture retention effect and excellent usability.

Other objects and advantages of the present invention will be apparent from the following description.

In accordance with the present invention, there is provided a cosmetic composition comprising (i) at least one compound selected from the group consisting of (a) water-soluble polyhydric alcohols having at least two hydroxyl groups in a molecule and (b) lecithins and (ii) at least bivalent metal salt of an organic acid.

DESCRIPTION OF THE PREFERRED EMBODIMENTS

The water-soluble polyhydric alcohols usable in the present invention should have two or more hydroxy groups in a molecule and include, for example, those containing two hydroxy groups such as propylene glycol, dipropylene glycol, tripropylene glycol, and other propylene glycols; 1,3-butylene glycol, 1,4-butylene glycol, and those containing three or more hydroxyl groups such as glycerol, diglycerol, triglycerol, tetraglycerol, and other polyglycerols; maltose, maltitose, sucrose, fructose, xylitol, sorbitol, maltotriose, threitol, erythritol, amylolyzed sugars, and reduced alcohol sugars may be used alone or in any mixture thereof. In particular, a more remarkable effect can be obtained exhibited in a cosmetic composition containing a polyhydric alcohol containing three or more hydroxy groups in a molecule.

The amount of the water-soluble polyhydric alcohol containing two or more hydroxyl groups in a molecule used in the present invention is preferably 5 to 40% by weight in the total amount of the cosmetic material. Especially, the effect of the present invention is remarkable in a cosmetic composition when the amount of the water-soluble polyhydric alcohol is within the range of 10 to 30% by weight. When the amount is less than 5% by weight, a sufficient moisture retention effect cannot be obtained and when the amount is over 40% by weight the stickiness cannot be sufficiently suppressed.

The lecithins usable in the present invention include, of course, lecithins extracted from egg yolk and plants (e.g. soybean, corn, cottonseed, rapeseed) and also include lecithins obtained by purifying those lecithins and the hydrogenation products thereof. In the present invention, one or more types of the above-mentioned lecithins may be suitably selected and used.

The amount of the lecithin used in the cosmetic composition according to present invention is preferably 0.001% to 5% by weight, preferably 0.01 to 2% by weight, in the total amount of the cosmetic composition. When the amount is less than 0.001% by weight, the desired effect is not sufficiently exhibited and when the amount is more than 5% by weight, the resultant cosmetic composition is not preferable in terms of the odor.

Examples of the organic acids for the bivalent metal salts of the organic acids usable in the present invention are amino acids such as aspartic acid and glutamic acid, pyrrolidonecarboxylic acid, lactic acid, citric acid, malic acid, tartaric acid, malonic acid, succinic acid, glutaric acid, fumaric acid and maleic acid. Examples of the bivalent metal are calcium and magnesium.

The amount of the bivalent metal salt of the organic acid in the present invention is preferably 0.001% by weight to 5% by weight, more preferably 0.003% by weight to 3% by weight, in the total amount of the cosmetic composition. When the amount is less than 0.001% by weight, the effect of suppressing the stickiness is not sufficient.

The cosmetic composition of the present invention, in addition to the above-mentioned essential components, may also optionally include any cosmetic components in such amounts that the effect of the present invention is not impaired. Examples of the other components conventionally used for cosmetic compositions are oil components (e.g., macademia nut oil, corn oil, olive oil, castor oil, jojoba oil, bees wax, fluid paraffin, squalane, petrolatum, micro crystalline wax, isopropyl mirystate), surfactants (e.g., polyoxyethylene castor oil, sorbitane fatty acid esters, glycerine fatty acid esters, polyoxyethylene sorbitatn fatty acid, polyoxyethylene glycerine fatty acid, triethanol amine salt of stearic acid potassium salt of oleic acid), ultraviolet absorbants (e.g., N,N-dimethyl PABA octyl ester, octyl methyl cinnamate, butyl methoxydibenzoylmethane, di-p-methoxycinnamic acid-mono-2-ehyl hexanoic acid glyceryl, 2-hydroxy-4-methoxy benzophenone, 2-hydroxy-4-methoxy benzophenone-5-sodium sulfonate), lower alcohols (e.g., ethyl alcohol, isopropyl alcohol), preservatives (e.g., methyl paraben, ethyl paraben, propyl paraben, butyl paraben, phenoxy ethanol), bactericides (e.g., chlorohexidine, hydrochloride, trichlorocarbanilide, triclosan, zinc pyrithione), coloring agents (e.g., dyes, pigments), powders, perfumes (e.g., essential oils, perfume of animal origin, synthetic pertume), medicines (e.g., vitamin A and its derivatives, vitamin E and its derivatives, vitamin C and its derivatives, pantothenic acid, vitamin H, vitamin B and its derivatives), water-soluble polymers (e.g., poly vinyl alcohol, polyvinyl pyrrolidone, carboxy vinyl polymer, xanthan gum, Hyaluronic acid), buffer agents (e.g., sodium glutamate, arginine, aspartic acid, citric acid, sodium citrate, lactic acid, sodium lactate).

Further, the present invention may be applied in any way, i.e., may be used for tonic, lotion, emulsion, cream, and other basic cosmetic compositions and also foundations and other makeup cosmetic compositions, hair treatments, and other hair cosmetic compositions.

The cosmetic compositions of the present invention containing polyhydric alcohols having two or more hydroxyl groups in a molecule and/or lecithins are superior in moisture retention effect and this suppresses the stickiness caused by water-soluble polyhydric alcohols and/or lecithins and the usability such as the suppleness given and affinity is improved. Further, the present cosmetic composition is excellent in stability and safety.

EXAMPLES

The present invention will now be further illustrated in detail by, but is by no means limited to, the following Examples, wherein "percents" are all by weight unless otherwise noted. The evaluation was carried out as follows.

Moistness and Lack of Stickiness

The sample prepared was used by a panel composed of 10 experts for an organoleptic test. The results are evaluated as follows:

⊚: Eight or more out of 10 members answered good o: Six or more out of 10 members answered good Δ: Four or more out of 10 members answered good x: Less than four out of 10 members answered good.

EXAMPLE 1 AND COMPARATIVE EXAMPLES 1 TO 4

Softening lotion was produced by an ordinary method by the formula shown in Table 1.

TABLE 1

| Component | Ex. 1 | Comp. Ex. 1 | Comp. Ex. 2 | Comp. Ex. 3 | Comp. Ex. 4 |
|---|---|---|---|---|---|
| Purified water | 74.38 | 89.88 | 77.38 | 91.88 | 76.88 |
| Glycerol | 10.0 | — | 10.0 | — | 10.0 |
| 1,3-Butylene glycol | 5.0 | — | 5.0 | — | 5.0 |
| Lactic acid | 2.0 | 2.0 | — | — | — |
| Calcium chloride | 0.5 | 0.5 | — | — | — |
| Carboxyvinyl polymer | 0.2 | 0.2 | 0.2 | 0.2 | 0.2 |
| Ethanol | 7.0 | 7.0 | 7.0 | 7.0 | 7.0 |
| Polyoxyethylene (60 mol) hydrogenated castor oil | 0.3 | 0.3 | 0.3 | 0.3 | 0.3 |
| Purified lecithin | 0.5 | — | — | 0.5 | 0.5 |
| Methyl paraben | 0.1 | 0.1 | 0.1 | 0.1 | 0.1 |
| Perfume | 0.02 | 0.02 | 0.02 | 0.02 | 0.02 |
| Moistness | ⊚ | x | o | o | o |
| Lack of stickiness | ⊚ | ⊚ | x | x | x |

As clear from Example 1, the cosmetic composition of the present invention is superior in moisture retention effect and further is free from stickiness.

| | % |
|---|---|
| (A) Cetyl alcohol | 5.0 |
| Stearic acid | 3.0 |
| Vaseline | 7.0 |
| Squalane | 10.0 |
| Isopropyl myristate | 2.0 |
| Glyceryl monostearate | 3.0 |
| Ethyl paraben | 0.2 |
| Hydrogenated lecithin | 1.0 |
| Perfume | 0.2 |
| (B) Glycerol | 20.0 |
| L-glutamic acid | 0.05 |
| Lactic acid | 0.1 |
| Magnesium chloride | 0.05 |
| Purified water | 48.2 |
| Potassium hydroxide | 0.2 |

Preparation Method

The oil phase portion (A) and the aqueous phase portion (B) were separately heated to 70° C. and completely melted, then the oil phase portion was mixed with the aqueous phase portion and emulsified by an emulsifier. The emulsion was cooled in a heat exchanger to a final temperature of 30° C. to obtain a nourishing cream.

EXAMPLE 3

Moisture Emulsion

| | % |
|---|---|
| A) Beeswax | 1.0 |
| Vaseline | 2.0 |
| Deodorized lanolin | 1.5 |
| Jojoba oil | 6.0 |
| Cetylisooctanoate | 4.0 |
| POE (60) hydrogenated castor oil | 2.0 |
| Purified lecithin | 1.0 |
| Ethyl paraben | 0.2 |
| Butyl paraben | 0.1 |
| Perfume | 0.3 |
| (B) Dipropylene glycol | 5.0 |
| Sorbitol | 10.0 |
| Lactic acid | 0.2 |
| Citric acid | 0.05 |
| Calcium chloride | 0.05 |
| Magnesium chloride | 0.1 |
| Xanthane gum (tradename: Keltroll T) | 0.05 |
| Carboxyvinyl polymer | 0.2 |
| Purified water | 66.15 |
| Potassium hydroxide | 0.1 |

Preparation Method

The moisture emulsion was prepared in the same manner as in Example 2.

EXAMPLE 4

Creamy Foundation

| | % |
|---|---|
| (A) Cetyl alcohol | 3.5 |
| Stearic acid | 2.0 |
| Deodorized lanolin | 5.0 |
| Squalane | 8.0 |
| Glyceryl monoisostearate | 2.5 |
| POE (10) behenyl ether | 0.5 |
| Yolk lecithin | 2.0 |
| Ethyl paraben | 0.2 |
| Butyl paraben | 0.2 |

|  | % |
|---|---|
| (B) Diglycerol | 3.0 |
| Xylitol | 5.0 |
| Calcium lactate | 2.0 |
| Pyrrolidone carboxylic acid | 0.1 |
| Citric acid | 0.1 |
| L-arginine | 0.5 |
| Mixed powder | 15.0 |
| Purified water | 50.15 |
| Potassium hydroxide | 0.25 |

Preparation Method

The foundation was prepared in the same manner as in Example 2.

The cosmetic compositions of Examples 2 to 4 were superior in moisture retention and were not sticky.

We claim:

1. A method of suppressing stickiness to the skin of a cosmetic composition containing (i) at least one compound selected from the group consisting of 5 to 40% by weight of at least one water-soluble polyhydric alcohol selected from the group consisting of propylene glycol, dipropylene glycol, tripropylene glycol, 1,3-butylene glycol, glycerol, diglycerol, triglycerol, tetraglycerol, maltose, maltitose, sucrose, fructose, xylitol, sorbitol, maltotriose, threitol, erythritol, amylolyzed sugars, and reduced alcohol sugars, which comprises incorporating in said composition (ii) 0.000–1 to 5% by weight of at least one bivalent metal salt of an organic acid selected from the group consisting of the calcium salts and the magnesium salts of aspartic acid, glutamic acid, pyrrolidone-carboxylic acid, lactic acid and citric acid, all based on the total weight of the cosmetic composition.

2. A method as claimed in claim 1, wherein the amount of the water-soluble polyhydric alcohol is 10% to 30% by weight, based on the total weight of the cosmetic composition.

3. A method as claimed in claim 1, wherein the amount of the bivalent metal salt of the organic acid is 0.003 to 3% by weight, based on the total weight of the cosmetic composition.

4. A method as claimed in claim 1, wherein the cosmetic composition further comprises 0.001 to 5% by weight of at least one lecithin selected from the group consisting of egg yolk lecithins and plant lecithins and the purified products thereof and the hydrogenation products thereof.

5. A method as claimed in claim 4, wherein the amount of the lecithin is 0.001% to 2% by weight, based on the total weight of the cosmetic composition.

* * * * *

UNITED STATES PATENT AND TRADEMARK OFFICE
CERTIFICATE OF CORRECTION

PATENT NO. : 5,709,849
DATED : January 20, 1998
INVENTOR(S) : Ito, et al.

It is certified that error appears in the above-identified patent and that said Letters Patent is hereby corrected as shown below:

Col. 6, line 3  Delete " 0.000-1 and substitute -- - 0.001 --

Signed and Sealed this

First Day of December, 1998

*Attest:*

BRUCE LEHMAN

*Attesting Officer*  *Commissioner of Patents and Trademarks*